United States Patent [19]

Juranas

[11] 4,273,557
[45] Jun. 16, 1981

[54] LIMULUS LYSATE PROCEDURE FOR DETERMINING ENDOTOXINS

[75] Inventor: David L. Juranas, St. Louis, Mo.

[73] Assignee: Mallinckrodt, Inc., St. Louis, Mo.

[21] Appl. No.: 135,810

[22] Filed: Mar. 31, 1980

[51] Int. Cl.$^3$ .................. C12Q 1/00; G01N 33/50
[52] U.S. Cl. .................. 23/230 B; 252/408; 435/4
[58] Field of Search .................. 23/230 B; 435/4; 252/408

[56] References Cited

U.S. PATENT DOCUMENTS

| | | | |
|---|---|---|---|
| 2,625,471 | 1/1953 | Mowry | |
| 3,944,391 | 3/1976 | Harris | 23/230 B |
| 3,959,128 | 5/1976 | Harris | |
| 4,038,029 | 7/1977 | Teller | 23/230 B |
| 4,096,091 | 6/1978 | Hopkins | 435/7 X |
| 4,107,077 | 8/1978 | Sullivan | 252/408 |

FOREIGN PATENT DOCUMENTS 1522127  8/1978  United Kingdom .

OTHER PUBLICATIONS

E. Hannecart-Pokorni et al., Eur. J. Biochem., 38 (1), 6–13 (1973).
K. J. Sweadner et al., Applied and Environmental Microbiology, 34 (4), 382–385 (1977).
F. C. McIntire et al., Biochemistry, 8 (10), 4063–4067 (Oct. 1969).
J. W. Shands, Jr. et al., J. Biol. Chem., 255 (3), 1221–1226 (1980).
J. A. Rudbach et al., Canadian Journal of Microbiology, 14, 1173–1178 (1968).
A. S. Michaels, Industrial and Engineering Chemistry, 46 (7), 1485–1490 (1954).
J. D. Sullivan, Jr. et al., Applied Microbiology, 28 (6), 1023–1026 (1974).

*Primary Examiner*—Sidney Marantz
*Attorney, Agent, or Firm*—Roy J. Klostermann

[57] ABSTRACT

A method and reagent for determining endotoxin in various fluids. The reagent comprises Limulus amebocyte lysate, a substantially linear polymeric water soluble interference-reducing agent and either calcium or magnesium cations.

9 Claims, No Drawings

LIMULUS LYSATE PROCEDURE FOR DETERMINING ENDOTOXINS

This invention relates to an improved Limulus lysate procedure for determining the presence of endotoxins and to improved lysate reagents.

The hemolymph of the horseshoe crab, Limulus Polyphemus, contains amebocytes. Lysis of these amebocytes liberates a substance which reacts with endotoxin to form a gel. This reaction between Limulus amebocyte lysate (hereinafter sometimes referred to as "LAL" or "lysate") and endotoxin has been made the basis for methods for detecting and/or determining endotoxin in a variety of fluids of pharmaceutical/medical interest. However, when this test is used to determine the presence of endotoxins in certain products such as lipid emulsions, salt solutions and blood plasma products, these products may alter the reacting of any endotoxins present making it less available to react with the lysate. This decrease in reactivity leads to improper detection of endotoxin in these products.

An object of this invention is to provide a LAL procedure suitable for detecting or determining the presence of endotoxin in products which tend to interfere with the reaction between endotoxin and LAL.

In accordance with this invention, there is provided an improvement in an in vitro test procedure for determining the presence of an endotoxin under endotoxin determining conditions by LAL in certain fluids which interfere with the reaction between any endotoxin present and LAL thereby giving an improper determination. The improvement comprises conducting said procedure in the presence of an interference reducing amount of a water soluble interference reducing agent to reduce said interference and sufficient divalent cation to overcome the chelating capacity of the interference reducing agent.

The fluids used in the practice of this invention are normally administered parenterally and include lipid emulsions for intravenous feeding, e.g., aqueous emulsions of vegetable oil, e.g. soybean oil available in concentrations of 5 to 30% by weight; salt solutions, e.g., parenterally administered sodium chloride solutions including sodium chloride for injection USP, sodium chloride for irrigation USP sodium chloride for inhalation and lactated Ringer's solution; and blood derivatives, e.g., normal serum albumin, available in 5%–25% w/v, plasma protein fraction and anti-hemophilic factor USP, immune globulin, Rho(D) immune globulin and antihuman globulin serum.

The interference reducing agents useful in this invention are polyelectrolytes having weight average molecular weights of at least 1,000, preferably 1,600 to 200,000 and more preferably 1,600 to 50,000 and having a substantially linear continuous carbon chain derived by the polymerization of an alaphatic unsaturated group. Thus, the polyelectrolytes of this type are ethylenic polymers having numerous side chains distributed along a substantially linear continuous carbon atom molecule. The side chains may be hydrocarbon groups, carboxylic acid groups or derivatives thereof, aminoalkyl groups, alkoxy groups and other organic groups, the number of which groups and the relative proportions of hydrophillic and hydrophobic groups being such as to provide a water soluble polymeric compound having a large number of ionizable radicals. The expression "water soluble" polymer as used herein includes those which form homogenous mixtures with water and the difficulty soluble polymers which expand in the presence of water and dissolve to at least some extent.

Suitable polyelectrolytic polymers are the polymers of acrylic acid derivatives, for example acrylic acid, the alkali metal, e.g. sodium, potassium, and ammonium salts of acrylic acid, acrylamide, acrylonitrile, the N-alkyl substituted amides, the N-aminoalkylamides, and the corresponding N-alkylaminoalkyl substituted amides, the aminoalkyl acrylates, the aminoalkyl methacrylamides and the N-alkyl substituted amino-alkyl esters of acrylic acids. These polymeric compositions may be the homopolymers or they may be copolymers with other copolymerizing monomers such as ethylene, propylene, isobutylene, styrene, alpha-methylstyrene, vinyl acetate, vinyl formate, alkyl ethers, acrylonitrile, methacrylonitrile, vinyl chloride, vinylidene chloride, the alkyl maleates, and the alkyl fumarates, and other olefinic monomers copolymers therewith. The aforementioned alkyl groups contain 1 to 6 carbon atoms. Copolymers of this type, having at least 20 mole percent, preferably 50 mole percent and more preferably 80 mole percent of the acrylic acid derivatives, are preferred, and especially when the comonomer is hydrophobic or has no ionic groups.

Polymers of this type may be prepared directly by the polymerization or copolymerization of suitable monomers, e.g. those containing a hydrophillic group such as carboxyl groups. Other polyelectrolytes polymers can be prepared by subsequent reactions of polymers and copolymers. For example, polymers containing nitrile groups may be hydrolyzed to form water soluble amide and carboxy containing polymers or hydrogenated to form amino containing polymers. When such polymers or copolymers are hydrolyzed, they are hydrolyzed to the extent of 25% to 100%, and preferably to the extent of at least 80% of groups that can by hydrolyzed.

Particular preferred polymers include polyacrylic acid having a weight average molecular weight of about 2000; copolymer of 75 mole % acrylic acid and 25 mole % acrylamide sodium salt, having a molecular weight of 1600; and an acrylonitrile copolymer around 50 mole % hydrolyzed with acid to form an acrylonitrile-acrylic acid copolymer.

When such polyelectrolytes are utilized in the acid form they are converted to the salt form during the LAL test procedure.

As stated, the aforementioned intereference reducing agent usually will chelate divalent cations. Thus, it is necessary to include a divalent cation to reduce or overcome the chelating capacity of the reducing agent. Usually, this is an amount sufficient to overcome this capacity generally from about 0.05–1.0 mole, preferably 0.1 to 0.5 mole, per mole of carboxyl groups of the interference reducing agent. This is in addition to any divalent cation utilized to increase the sensitivity of the lysate discussed below. Normally, the divalent cation is combined with the interference reducing agent. Thus in the case of an alkali metal salt interference reducing agent, combination with the divalent cation forms a mixed salt, e.g. sodium calcium salt of a copolymer of about 75 mole % acrylic acid and about 25 mole % acrylamide having a molecular weight of 1600.

In accordance with the reagent of the present invention there is provided a reagent containing LAL of suitable sensitivity of at least 0.25 nanogram per ml with US reference endotoxin EC-2 standard, an interference reducing amount of one of the aforementioned interference reducing agents and sufficient divalent cation to overcome the chelating capacity of the reducing agent. This reagent is preferably lyophylized.

LAL may be prepared according to the procedure, described in British Pat. No. 1,522,127 which is incorporated herein by reference.

For example, the hemolymph from healthy specimens of Limulus polyphemus is collected in a saline anticoagulant solution generally as described by Levin and Bang—"Clottable Protein in Limulus: Its Localization and Kinetics of Its Coagulation by Endotoxin", Thromb. Diath. Haemorrh 19: 186–197 (1968)—The amebocytes are collected and washed with the saline anticoagulant solution and centrifuged.

The separated amebocytes are suspended in water and the osmotic disruption of the cells is complemented by multiple exposures to mechanical agitation. The cellular debris is separated from the lysate by means of a centrifuge and the lysate fractions are pooled and stored at 0°–4° C.

The sensitivity of the lysate toward endotoxin is adjusted to the desired level of sensitivity by dilution or by mixing with another batch of lysate of different sensitivity. The solution is generally buffered to the pH range 6.5–7.5 by means of a suitable buffer, e.g. tromethamine [tris-(hydroxymethyl) aminomethane" and tromethamine hydrochloride.

The buffered lysate solution, prepared as described above, is subdivided into serum vials, e.g. containing 1.2 or 5.2 ml of the solution, and the subdivided solution is lyophilized. After lyophilization the vials are sealed and refrigerated.

The lyophilized lysate has the form of a white powder or a white, frangible pellet.

Sensitivity of the lysate toward endotoxin is increased by including low concentrations of divalent and monovalent cations. Calcium ions are the preferred divalent ions, although other alkaline earth ions such as magnesium ions or other divalent ions may be used. Sodium ions are the preferred monovalent ions, but other monovalent ions, especially alkali metal ions such as lithium ions may be used. The chlorides ($CaCl_2$, NaCl, etc.) are convenient sources of these added ions, although other salts may be used. Preferably these electrolytes are added in endotoxin sensitivity increasing amounts e.g. such that when the lyophilized lysate is reconstituted the divalent cation (e.g., $Ca^{+2}$) concentration will be in the range of 0.0001–0.1 molar and the monovalent cation (e.g., $Na^+$) concentration will be in the range of 0.001–0.1 molar.

All of the above operations described are carried out under conditions such as to insure that the final product is sterile and free of endotoxin. Methods of insuring freedom from endotoxins are known to the art. For example, inorganic additives ($CaCl_2$, NaCl) may be rendered endotoxin-free by heating the dry salts at 250° C. for at least 120 minutes. Organic additives, because of their melting points, etc. must ordinarily be dissolved, and the solution autoclaved at 121° C. for 60 minutes or more to destroy any endotoxins present.

A general description of the procedure for determining endotoxins may be found in the aforementioned British Patent.

Usually lyophilized lysate is reconstituted with sufficient sterile, pyrogen free water. It is displaced in aliquot portions, e.g. 0.1 ml in test tubes and mixed with an equal amount of the liquid being tested for endotoxin. Formation of a gel indicates the presence of endotoxin.

This procedure is carried out under endotoxin determining conditions utilizing a sufficient amount of lysate, e.g., 0.01 to 1 ml of reconstituted lysate of suitable activity, e.g. 0.01 to 0.25 ng/ml US reference endotoxin EC-2. Such conditions include suitable reaction times, e.g. 10 minutes to 60 minutes, reaction temperature e.g. 36° C. to 40° C., use of a buffer, e.g. Tris HCL to maintain the pH from about 6.0 to 8.0 during the determination.

In accordance with the present invention the interference reducing agent is present during the lysate endotoxin reaction, preferably during the whole reaction. Advantageously, the interference reducing agent is added to the liquid to be tested before the lysate or is incorporated in the LAL reagent before lyophilization. It is used in interference reducing amounts, for example, in the case where it is added to the lysate prior to testing it is used in an amount of from 0.05% w/v to 3.0% w/v preferably 0.4% w/v based on total volume of test sample and in the case where it is incorporated into the reagent and lyophillized it is used in an amount of from about 0.05% w/v to about 3.0% w/v, preferably 0.4% w/v, based on the volume of lysate solution.

The following examples illustrate the invention. All parts are by weight unless otherwise stated.

EXAMPLES

All of the operations described are carried out under conditions such as to insure that the final product is sterile and free of endotoxin.

EXAMPLE 1

The hemolymph from healthy specimens of Limulus polyphemus is collected in a saline anticoagulant solution generally as described by Levin and Bang (1969—see above). The amebocytes are collected and washed with the saline anticoagulant solution in a centrifuge.

The separated amebocytes are suspended in water and the osmotic disruption of the cells is completed by multiple exposures to mechanical agitation. The cellular debris is separated from the lysate by means of a centrifuge and the lysate fractions are pooled and stored at 0°–4° C.

The sensitivity of the lysate toward endotoxin is adjusted to the desired level of sensitivity. The solution is buffered to the pH range of 6.5–7.5 by means of tromethamine [tris-(hydroxymethyl)aminomethane] and tromethamine hydrochloride and is made 0.01 molar in calcium chloride, 0.077 molar in sodium chloride, all of the additives having previously been rendered free of endotoxins.

The buffered lysate (I) is then subdivided into serum vials, each containing 5.2 ml of the solution, and then the subdivided solution is lyophilized. After lyphilization, the vials are sealed and refrigerated.

The interference reducing agent (II) is prepared by adding 5 ml of Sterile Water for Injection USP, 50 mg of $Ca(OH)_2$ to 5 ml of 43% w/v polyacrylic acid—polyacrylamide copolymer (75 mole % acid 25 mole % acrylamide) sodium salt in water, M.W. 1,600. This solution is autoclaved for 30 minutes at 121° C. to depyrogenate and is then adjusted to pH 7.5 with 0.2 ml 12 N HCl. 4.0 ml of II was then added to 200 ml of the buffered lysate (I) solution, prepared as described above, prior to lyophilization. The resulting interference reducing lysate solution (III) is then subdivided into serum vials, each containing 5.2 ml. of the solution, and the subdivided solution is lyophilized. After lyophilization the vials are sealed and refrigerated.

The following operations were carried out under conditions designed to insure asepsis and freedom from the extraneous introduction of endotoxin.

Serially diluted endotoxin solutions were prepared from E. coli 055:B5 endotoxin in each of the following solutions, Sterile Water for Injection USP; 20% lipid emulsion; (Intra Lipid Marketed by Cutter Labs) and plasma protein fraction (Marketed by Cutter Labs). These serially diluted endotoxin samples were then tested with both lysate (I) and interference reducing lysate (III). The tests were performed by reconstituting lysates (I) and (III) with 5.2 ml of Sterile Water for Injection USP followed by gently swirling for a few seconds to completely dissolve the residue. Aliquots of 0.1 ml of the reconstituted lysates (I) and (III) were dispensed into 10 mm×75 mm test tubes; to each tube was added 0.1 ml from the appropriate serially diluted endotoxin solutions prepared above. The tubes were swirled gently to mix and then incubated undisturbed at 37° C. for 60 minutes.

At the end of this time, a titer was determined as the lowest concentration of endotoxin which gave a positive result in the LAL test. A test is scored as positive if the lysate formed a clot which would maintain its integrity when the tube was inverted 180°, negative if the gel broke before the full inversion of 180°. As is customary in the art, fluids which do not interfere with endotoxin detection by LAL would yield a titer which is not different from the Sterile Water for Injection USP titer by plus or minus one twofold dilution.

The test results for endotoxin concentrations in the appropriate solutions are set forth below:

TABLE I

| Solution Tested | Titer with Lysate (I) | Titer with Interference Reducing Lysate (III) |
|---|---|---|
| Sterile WFI USP | 25 pg/ml | 25 pg/ml |
| 20% Lipid Emulsion | >100 pg/ml | 50 pg/ml |
| Plasma Protein Fraction | >100 pg/ml | 50 pg/ml |

EXAMPLE 2

Lysate (I) and interference reducing (II) were prepared as previously described in Example 1.

Serially diluted endotoxin solutions were prepared from either E. coli 055:B5 endotoxin. or US reference endotoxin EC-2 in one or more of the following solutions: Sterile Water for Injection USP; 5% Albumin (Cutter Labs); 0.9% NaCl USP (Travenol); 10% lipid emulsion (Cutter); and plasma protein fraction (Cutter). A sample was removed from each of the appropriate serially diluted solutions and tested with Lysate (I). After these samples were removed, interference reducing agent (II) was added to give a final concentration of 2% v/v (0.1 ml of II plus 5 ml sample). The solutions were mixed thoroughly and then once again tested with lysate (I).

The test results for endotoxin concentrations in the appropriate solutions are set forth below.

TABLE 2

| Solution Tested | 055:B5 Endotoxin | | EC-2 Endotoxin | |
|---|---|---|---|---|
|  | w/o II | w/2% II | w/o II | w/2% II |
| Sterile WFI USP | 50 pg/ml | 25 pg/ml | 60 pg/ml | 30 pg/ml |
| 10% lipid emulsion | >100 pg/ml | 25 pg/ml | * | * |
| Plasma Protein Fraction | >100 pg/ml | 25 pg/ml | >250 pg/ml | 30 pg/ml |
| 5% Albumin | >100 pg/ml | 25 pg/ml | >250 pg/ml | 30 pg/ml |
| Saline USP | * | * | >250 pg/ml | 60 pg/ml |

*not tested

EXAMPLE 3

Lysate (I) was prepared as previously described in Example 1.

Polyacrylic acid-acrylonitrile copolymer about 50 mole % hydrolized (IV) was prepared by adding 15 ml of $H_2O$ and 50 ml concentrated $H_2SO_4$ to 2 gm of polyacrylonitrile in a 100 ml beaker. The solution was mixed for 20 hours at 25° C. with a magnetic spin bar. The resulting polymer (IV) was then precipitated by the addition of 100 ml of ethanol. The solid was collected by centrifugation and washed 4 times with 200 ml of ethanol. The resulting polymer (IV) was then dried at 60° C. under vacuum for 8 hours.

Interference reducing agent (V) was prepared by dissolving 50 mg of polymer (IV) in a solution of 10 ml $H_2O$ and 0.5 ml 5 N NaOH. To this solution was added 25 mg $Ca(OH)_2$ and then the resulting mixture was autoclaved for 30 minutes at 121° C. The solution was cooled and pH adjusted to pH 7.0 with 12 N HCl.

A serially diluted endotoxin was prepared from US reference endotoxin EC-2 in 0.9% normal saline USP (Travenol) and Sterile Water for Injection USP. The appropriate serially diluted endotoxin solutions were then tested with lysate (I) as described in Example 1. After the serially diluted endotoxin solutions were tested with lysate (I). Interference reducing agent (V) was added to a final concentration of 10% v/v (0.6 ml of V + 5 ml of sample). The solutions were mixed thoroughly and once again tested with lysate (I).

The test results are set forth below:

TABLE 3

| Sample Tested | Titer without V | Titer with 10% V |
|---|---|---|
| Sterile WFI USP | 30 pg/ml | 30 pg/ml |
| 0.9% Normal Saline USP | 500 pg/ml | 125 pg/ml |

EXAMPLE 4

Lysate was prepared as previously described in Example 1.

Interference reducing agent (VI) was prepared by mixing 25 ml of a 65% polyacrylic acid-$H_2O$ solution (m.w. 2,000) with 75 ml of $H_2O$, 7.5 gm of NaOH and 107 mg $Ca(OH)_2$. The solution was autoclaved for 30 minutes at 121° C. and then the pH was adjusted to pH=8.0 with 5 N HCl.

A serially diluted endotoxin solution was prepared from US reference endotoxin EC-2 in 0.9% normal saline UPS and Sterile Water for Injection USP. The appropriate serially diluted endotoxin solutions were then tested with Lysate (I) as described in Example I. After the serially diluted endotoxin solutions were tested with Lysate (I), interference reducing agent (VI)

was added to a final concentration of 7% and once again tested with Lysate (I).

The test results are set forth below:

TABLE 4

| Sample tested | Titer without VI | Titer with VI |
|---|---|---|
| Sterile WFI USP | 30 pg/ml | 30 pg/ml |
| 0.9% normal saline USP | 500 pg/ml | 30 pg/ml |

EXAMPLE 5

Lysate (I) was prepared as previously described in Example 1.

Interference reducing agent (VII) was prepared by dissolving 2.1 gm of acrylic acid-acrylamide copolymer (M.W. 200,000) into a solution of 19 ml water for injection and 100 mg $(Ca(OH)_2)$. The solution was mixed until all solids were dissolved and then the pH was adjusted to pH=8.0 with 0.7 ml of 5 N HCl.

A serially diluted endotoxin solution was prepared from US reference endotoxin EC-2 in 0.9% Normal Saline USP and sterile water for injection USP. The appropriate serially diluted endotoxin solutions were then tested with lysate (I) as described in Example 1. After the serially diluted endotoxin solutions were tested with lysate (I), interference reducing agent (VII) was added to a final concentration of 4% v/v (0.2 ml of VII+5 ml of sample). The solutions were mixed thoroughly and once again tested with lysate (I).

The test results are set forth below:

TABLE 5

| Sample tested | Titer without VII | Titer with VII |
|---|---|---|
| Sterile WFI USP | 60 pg/ml | 30 pg/ml |
| 0.9% Normal Saline USP | 500 pg/ml | 30 pg/ml |

What is claimed:

1. In an in vitro test method for determining endotoxin under endotoxin determining conditions by Limulus amebocyte lysate in certain fluids selected from the group consisting of lipid emulsions for injection, parenterally administered sodium chloride solutions, lactated Ringer's solution, normal serum albumin, plasma protein fraction and anti-hemophilic factor USP which interferes with the reaction between any endotoxin present and said lysate thereby giving an improper determination, the improvement comprising conducting said method in the presence of (1) an interference reducing amount of a substantially linear polymeric water soluble interference reducing agent to reduce said interference, said agent having a molecular weight of at least 1000 selected from the group consisting of acrylic acid-acrylamide copolymer, acrylic acid—acrylonitrile copolymer, polyacrylic acid, alkali metal salts of polyacrylic acid, hydrolyzed polyacrylamide, alkali metal salts of hydrolyzed polyacrylamide, hydrolyzed polyacrylonitrile and alkali metal salts of polyacrylonitrile and (2) a sufficient amount of divalent cation selected from the group consisting of calcium and magnesium to overcome the chelating capacity of said interference reducing agent.

2. A method according to claim 1, wherein the interference reducing agent is present in an amount of from about 0.05% to about 3% w/v and the divalent cation is present in an amount from about 0.05%–1.0 mole per mole of carboxyl groups of said interference reducing agent.

3. A method according to claim 2, wherein the interference reducing agent is selected from the group consisting of polyacrylic acid, polyacrylic acid sodium salt, a copolymer of acrylic acid and acrylamide, hydrolyzed polyacrylamide, the sodium salt of hydrolyzed polyacrylamide, hydrolyzed polyacrylonitrile and the sodium salt of hydrolyzed polyacrylonitrile and wherein the divalent cation is calcium.

4. A method according to claim 3, wherein the fluid is selected from the group consisting of lipid emulsions for injection.

5. A method according to claim 3, wherein the fluid is selected from the group consisting of parenterally administered sodium chloride solutions.

6. A method according to claim 3, wherein the fluid is selected from the group consisting of normal serum albumin, plasma protein fraction and anti-hemophilic factor.

7. An in vitro test reagent for determining endotoxin comprising Limulus amebocyte lysate having a sensitivity of at least about 0.25 mg/ml with US reference endotoxin EC-2, an interference reducing amount of a substantially linear polymeric water soluble interference reducing agent having a molecular weight of at least 1000 selected from the group consisting of acrylic acid-acrylamide copolymer, acrylic acid-acrylonitrile copolymer, polyacrylic acid, alkali metal and ammonium salts of polyacrylic acid, hydrolyzed polyacrylamide, alkali metal and ammonium salts of hydrolyzed polyacrylamide, hydrolyzed polyacrylonitrile and alkali metal and ammonium salts of polyacrylonitrile and a sufficient amount of divalent cation selected from the group consisting of calcium and magnesium.

8. A reagent according to claim 7, wherein the interference reducing agent is present in an amount of from about 0.05% to about 3% w/v.

9. A reagent according to claim 8, wherein the interference reducing agent is selected from the group consisting of polyacrylic acid, the sodium salt thereof, a copolymer of acrylic acid and acrylamide, hydrolyzed polyacrylamide, the sodium salt thereof, hydrolyzed polyacrylonitrile and the sodium salt thereof.

* * * * *